US008241617B2

(12) United States Patent
Chen et al.

(10) Patent No.: US 8,241,617 B2
(45) Date of Patent: Aug. 14, 2012

(54) METHODS FOR REMOVING MAKE-UP COMPOSITIONS FROM KERATIN MATERIALS

(75) Inventors: Michell Chen, Centereach, NY (US); Victoria Chou, Edison, NJ (US); Padraig McDermott, Westerfield, NJ (US)

(73) Assignee: L'Oréal, Paris (FR)

( * ) Notice: Subject to any disclaimer, the term of this patent is extended or adjusted under 35 U.S.C. 154(b) by 1551 days.

(21) Appl. No.: 11/193,444

(22) Filed: Aug. 1, 2005

(65) Prior Publication Data

US 2007/0041928 A1 Feb. 22, 2007

(51) Int. Cl.
*A61K 8/898* (2006.01)
*A61Q 19/10* (2006.01)
*A61Q 1/14* (2006.01)

(52) U.S. Cl. ............... 424/70.122; 424/64; 510/130; 510/136

(58) Field of Classification Search .................. None
See application file for complete search history.

(56) References Cited

U.S. PATENT DOCUMENTS

| | | | |
|---|---|---|---|
| 2,823,195 A | 2/1958 | Shorr et al. | |
| 2,823,218 A | 2/1958 | Speier et al. | |
| 3,723,566 A | 3/1973 | Thompson et al. | |
| 4,322,400 A | 3/1982 | Yuhas | |
| 4,822,852 A | 4/1989 | Wittmann et al. | |
| 5,262,505 A | 11/1993 | Nakashima et al. | |
| 5,407,986 A | 4/1995 | Furukawa et al. | |
| 5,412,004 A | 5/1995 | Tachibana et al. | |
| 5,473,041 A | 12/1995 | Itoh | |
| 5,512,272 A | 4/1996 | Krzysik | |
| 5,567,428 A | 10/1996 | Hughes | |
| 5,725,882 A | 3/1998 | Kuman et al. | |
| 5,800,816 A * | 9/1998 | Brieva et al. ............. | 424/63 |
| 5,837,223 A | 11/1998 | Barone et al. | |
| 5,874,069 A | 2/1999 | Mendolia et al. | |
| 5,919,441 A | 7/1999 | Mendolia et al. | |
| 5,969,172 A | 10/1999 | Nye | |
| 5,981,680 A * | 11/1999 | Petroff et al. ............. | 528/26 |
| 5,985,297 A | 11/1999 | Mellul et al. | |
| 6,045,782 A | 4/2000 | Krog et al. | |
| 6,051,216 A | 4/2000 | Barr et al. | |
| 6,060,072 A | 5/2000 | Konik et al. | |
| 6,103,250 A | 8/2000 | Brieva et al. | |
| 6,177,091 B1 | 1/2001 | Bara et al. | |
| 6,353,076 B1 | 3/2002 | Barr et al. | |
| 6,362,287 B1 | 3/2002 | Chorvath et al. | |
| 6,362,288 B1 | 3/2002 | Brewer et al. | |
| 6,376,078 B1 | 4/2002 | Inokuchi | |
| 6,406,683 B1 * | 6/2002 | Drechsler et al. ......... | 424/64 |
| 6,423,324 B1 | 7/2002 | Murphy et al. | |
| 6,426,062 B1 | 7/2002 | Chopra et al. | |
| 6,451,295 B1 * | 9/2002 | Cai et al. ................ | 424/65 |
| 6,503,632 B1 | 1/2003 | Hayashi et al. | |
| 6,524,598 B2 | 2/2003 | Sunkel et al. | |
| 6,541,017 B1 | 4/2003 | Lemann et al. | |
| 6,569,955 B1 | 5/2003 | Brewer et al. | |
| 6,682,748 B1 | 1/2004 | De La Poterie et al. | |
| 6,916,464 B2 | 7/2005 | Hansenne et al. | |
| 2002/0015684 A1 * | 2/2002 | Vatter ..................... | 424/70.12 |
| 2002/0028223 A1 | 3/2002 | Vatter et al. | |
| 2002/0048557 A1 | 4/2002 | Cai et al. | |
| 2002/0051758 A1 | 5/2002 | Cai et al. | |
| 2002/0114773 A1 * | 8/2002 | Kanji et al. ............... | 424/70.21 |
| 2003/0068348 A1 | 4/2003 | Ferrari et al. | |
| 2003/0072730 A1 | 4/2003 | Tournilhac | |
| 2003/0082129 A1 | 5/2003 | Buckingham et al. | |
| 2003/0170188 A1 | 9/2003 | Ferrari et al. | |
| 2003/0228333 A1 | 12/2003 | Fecht et al. | |
| 2003/0232030 A1 | 12/2003 | Lu et al. | |
| 2003/0235548 A1 | 12/2003 | Lu | |
| 2003/0235552 A1 | 12/2003 | Yu | |
| 2003/0235553 A1 | 12/2003 | Lu et al. | |
| 2004/0001799 A1 | 1/2004 | Lu et al. | |
| 2004/0115153 A1 | 6/2004 | Yu | |
| 2004/0115154 A1 | 6/2004 | Yu | |
| 2004/0120912 A1 | 6/2004 | Yu | |
| 2004/0126336 A1 | 7/2004 | Hansenne et al. | |
| 2004/0170586 A1 * | 9/2004 | Ferrari et al. ............. | 424/63 |
| 2004/0180032 A1 | 9/2004 | Manelski et al. | |
| 2004/0197285 A1 | 10/2004 | Van Dort | |
| 2004/0223936 A1 | 11/2004 | Fecht et al. | |
| 2005/0009989 A1 | 1/2005 | Liew et al. | |

(Continued)

FOREIGN PATENT DOCUMENTS

EP 0 377 447 A2 7/1990

(Continued)

OTHER PUBLICATIONS

U.S. Appl. No. 11/342,748, filed Jan. 31, 2006, Blin, et al.

(Continued)

*Primary Examiner* — Frederick Krass
*Assistant Examiner* — Isaac Shomer
(74) *Attorney, Agent, or Firm* — Oblon, Spivak, McClelland, Maier & Neustadt, L.L.P.

(57) ABSTRACT

The invention relates to kits and methods for removing a long wearing or transfer resistant make-up composition from keratin materials such as eyelashes, nails, skin or lips, wherein the make-up composition contains at least one oil soluble film-forming agent and at least one coloring agent, including applying to the make-up composition a removal composition containing at least one oil soluble film-forming agent and at least one oil and removing the make-up composition from the eyelashes, nails, skin or lips.

18 Claims, No Drawings

U.S. PATENT DOCUMENTS

| | | |
|---|---|---|
| 2005/0020769 A1 | 1/2005 | Lu et al. |
| 2005/0089492 A1 | 4/2005 | Lu et al. |
| 2005/0158260 A1 | 7/2005 | Ferrari et al. |
| 2008/0171008 A1 | 7/2008 | Bui |

FOREIGN PATENT DOCUMENTS

| | | |
|---|---|---|
| EP | 0 594 285 A2 | 4/1994 |
| EP | 0 693 517 A1 | 1/1996 |
| EP | 0 709083 | 5/1996 |
| EP | 1 048 686 | 11/2000 |
| GB | 134 8783 | 3/1974 |
| WO | WO 97/36572 | 10/1997 |
| WO | WO 97/36573 | 10/1997 |
| WO | WO 99/06473 | 2/1999 |
| WO | WO99/22710 | 5/1999 |
| WO | WO 01/09239 A1 | 2/2001 |
| WO | WO 01/97758 A2 | 12/2001 |
| WO | WO 0197758 A2 | 12/2001 |
| WO | WO 02/17870 A2 | 3/2002 |
| WO | WO 02/17871 A2 | 3/2002 |
| WO | WO 02/089760 A1 | 11/2002 |
| WO | WO 03/013447 A2 | 2/2003 |
| WO | WO 03/105788 A2 | 6/2003 |
| WO | WO 03/101412 A2 | 12/2003 |
| WO | WO 03105788 A2 * | 12/2003 |
| WO | WO 2004/054523 | 7/2004 |
| WO | WO 2004/054524 | 7/2004 |

OTHER PUBLICATIONS

Notice of Rejection for Japanese Patent Application 2004-512707 issued Jun. 6, 2006 (w/English Translation).

U.S. Appl. No. 60/438,782, filed Jan. 9, 2003, Tournilhac.
U.S. Appl. No. 60/438,770, filed Jan. 9, 2003, Blin.
U.S. Appl. No. 60/528,698, filed Dec. 12, 2003, Lu et al.
U.S. Appl. No. 60/528,696, filed Dec. 12, 2003, Lu, et al.
U.S. Appl. No. 60/528,700, filed Dec. 12, 2003, Ferrari, et al.
U.S. Appl. No. 60/620,689, filed Oct. 22, 2004, Lu.
U.S. Appl. No. 09/395,613, filed Sep. 14, 1999, Ferrari.
U.S. Appl. No. 10/538,920, filed Jun. 13, 2005, Blin, et al.
U.S. Appl. No. 10/538,924, filed Jun. 13, 2005, Tournilhac, et al.
U.S. Appl. No. 11/193,444, filed Aug. 1, 2005, Chen, et al.
U.S. Appl. No. 10/517,390, filed Dec. 10, 2004, Ferrari, et al.
U.S. Appl. No. 11/024,471, filed Dec. 30, 2004, Blin, et al.
U.S. Appl. No. 11/217,293, filed Sep. 2, 2005, Bui, et al.
Dow Corning® 2-8178 Gellant, Ref. No. 27-1055-01, Aug. 2002, 35 pp.
Dow Corning® 2-8178 Gellant, Product Information Personal Care, 6 pp.
Shin-Etsu Silicones for Personal Care; Product Brochure, KSP-100•101•102•103•104•105 "Hybrid Silicone Powders for Personal Care".
Shin-Etsu Silicones for Personal Care; Product Brochure, KSP-200•300 "Hybrid Silicone Powders containing Fluoroalkyl or Phenyl group for Personal Care".
English Language Derwent Abstract of EP 0 923 928, Jun. 23, 1999.
English Language Derwent Abstract of EP 1 068 856, Jan. 17, 2001.
English Language Derwent Abstract of FR 2 765 800, Jan. 15, 1999.
Dow Corning 2-8178 Gellant, Ref. No. 27-1055B-01, Apr. 16, 2003, 6 pp.
U.S. Appl. No. 11/254,919, filed Oct. 21, 2005, Lu, et al.
U.S. Appl. No. 12/648,020, Dec. 28, 2009, Yu.

* cited by examiner

METHODS FOR REMOVING MAKE-UP COMPOSITIONS FROM KERATIN MATERIALS

FIELD OF THE INVENTION

The present invention relates to kits and methods for removing long-wear or transfer-resistant make-up compositions from keratin materials such as eyelashes, nails, skin or lips, wherein the make-up composition comprises at least one oil soluble film-forming agent and at least one coloring agent, comprising applying to the make-up composition a removal composition comprising at least one oil soluble film-forming agent and at least one oil and removing the make-up composition from the keratin materials.

DISCUSSION OF THE BACKGROUND

Many pigmented cosmetic compositions such as foundations, lipsticks and mascaras have been developed for longer wear and transfer resistance properties. This is typically accomplished by the use of compositions that form a film after application. Such compositions generally contain volatile solvents which evaporate on contact with the skin or other keratinous tissue, leaving behind a film or layer comprising waxes and/or resins, pigments, fillers, and actives.

Removal of such transfer resistant compositions has been problematic. Typically, such transfer-resistant compositions have been removed using removal compositions which are solvent-based (for example, mineral oil) or which contain substantial amounts of volatile oils. However, using such removal compositions typically leads to a harsh, somewhat abrasive removal process, leaving an uncomfortable, dry and/or chapped feeling on the keratin material from which the transfer resistant composition has been removed. For example, using solvent-based or volatile oil-based removal compositions can lead to insufficient film disruption of the transfer resistant composition, meaning that aggressive rubbing or wiping is necessary to remove the transfer resistant composition from the keratin material which, in turn, can lead to raw, dry, chapped, sensitive keratin materials. Similarly, volatile oil-based removal compositions, due to their evaporative nature, can lead the keratin materials feeling dry, chapped and sensitive.

Thus, there remains a need for improved methods for removing long-wearing cosmetic compositions which transfer little or not at all from keratin materials such as skin, lips or eyelashes.

Accordingly, one aspect of the present invention is to provide kits and methods for removing long wearing or transfer-resistant compositions from keratin materials which are able to address or overcome at least some of the aforementioned problems with previous removal methods.

SUMMARY OF THE INVENTION

The present invention relates to methods for removing cosmetic compositions, preferably long wearing or transfer-resistant make-up compositions, from keratin materials such as eyelashes, nails, skin or lips, wherein the make-up composition comprises at least one oil soluble film-forming agent and at least one coloring agent, comprising applying to the make-up composition a removal composition comprising at least one oil soluble film-forming agent and at least one oil and removing the make-up composition from the keratin materials.

The present invention also relates to kits comprising a transfer-resistant or long wearing make-up composition comprising at least one oil soluble film-forming agent and at least one coloring agent and a removal composition comprising at least one oil soluble film-forming agent and at least one oil. Such kits can also include additional compositions such as, for example, topcoats for application to the long wearing or transfer resistant make-up composition or primers (basecoats) for application to keratin materials prior to application of a long wearing or transfer resistant make-up composition.

The present invention also relates to methods for applying gloss to keratin materials comprising applying a gloss composition comprising at least one oil soluble film-forming agent, at least one oil and at least one coloring agent to the keratin material in an amount sufficient to provide gloss to the keratin material.

DETAILED DESCRIPTION OF THE INVENTION

As used herein, the expression "at least one" means one or more and thus includes individual components as well as mixtures/combinations.

"Film former" or "film forming agent" as used herein means a polymer that, after dissolution in at least one solvent, leaves a film on the substrate to which it is applied, for example, once the at least one solvent evaporates, absorbs and/or dissipates on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred from a wearer to any other substrate, such as transfer from the neck of an individual to a collar after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. Further, the amount transferred may be compared with that transferred by other compositions, such as commercially available compositions. In a preferred embodiment of the present invention, little or no composition is transferred to the substrate. Thus, transfer-resistant compositions include transfer-free compositions.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (including lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Make-up composition" as used herein means any composition applied to keratin materials for aesthetic purposes. Examples of acceptable make-up compositions include, but are not limited to, lip compositions such as lipsticks, liquid lip colors, lip glosses, skin compositions such as foundations, fingernail compositions such as nail polish and eyelash/hair compositions such as mascaras.

The cosmetic compositions, kits and methods of the present invention can comprise, consist of, or consist essentially of the essential elements and limitations of the invention described herein, as well as any additional or optional ingredients, components, or limitations described herein or otherwise useful in personal care compositions intended for topical application to the skin.

The make-up, removal or gloss compositions of the present invention may be in any form. For example, they may be a paste, a solid, a gel, or a cream. They may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. The compositions can also be in a form chosen from a translucent anhydrous gel and a transparent anhydrous gel. The compositions of the invention may, for example, comprise an external or continuous fatty phase. The compositions may be anhydrous. In another embodiment, the compositions of the invention may be transparent or clear. The compositions can also be a molded composition or cast as a stick or a dish. The compositions in one embodiment can be a solid such as a molded stick or a poured stick.

In accordance with preferred embodiments of the present invention, methods for removing a transfer-resistant or long wearing make-up composition from eyelashes, skin, nails or lips, wherein the make-up composition comprises at least one oil soluble film-forming agent and at least one coloring agent, comprising applying to the make-up composition a removal composition comprising at least one oil soluble film-forming agent and at least one oil and removing the make-up composition from the eyelashes, skin, nails or lips are provided. Preferred methods allow for gentle, comfortable removal of long wearing or transfer resistant make-up compositions from keratin materials. Preferred methods can also provide the keratin material with a pleasing cushiony, bouncy feel during and/or after the removal process.

Without being bound to any particular theory, Applicants believe that when the removal composition is applied to the make-up composition, it forms a layer (for example, a cushiony layer) on top of the make-up composition, and that these two layers are compatible. It is believed that the removal composition breaks down the make-up composition, particularly the film remaining on the keratin material after application of the make-up composition, through compatible interaction between the two layers. It is further believed that the compatible interaction between the two layers results at least in part from the presence of oil soluble film forming agents in both the make-up composition and the removal composition. After the removal composition has sufficiently broken down the make-up composition, the make-up composition can be easily removed by non-vigorous rubbing, wiping, etc.

Long wearing or Transfer Resistant Make-up Composition

According to preferred embodiments of the present invention, the long wearing or transfer resistant make-up composition comprises at least one oil soluble film forming agent and at least one coloring agent.

In the make-up composition, any oil soluble film forming agent can be used. For example, suitable oil soluble film forming agents include, but are not limited to, the film forming agents disclosed in U.S. patent application publication no. 2004-0170586, corresponding to U.S. patent application Ser. No. 10/733,467, filed Dec. 10, 2003, hereby incorporated by reference in its entirety. This disclosure includes, but is not limited to, polyorganosiloxane-containing polymers, silicone resins (for example, "MDTQ" resins like MQ or MK resins), and silicone acrylate polymers.

Preferably, the oil soluble film forming agent is a polyorganosiloxane containing polymer or copolymer. Most preferably, the oil soluble film forming agent is a polysilicone polyamide polymer such as, for example, those disclosed in U.S. Pat. Nos. 5,874,069, 5,919,441, 6,051,216 and 5,981,680, all of which are hereby incorporated by reference in their entirety, and/or those polymers described below.

Preferred polyorganosiloxane containing polymers are chosen from homopolymers and copolymers, preferably, with a weight-average molecular mass ranging from about 500 to about $2.5 \times 10^6$ or more, comprising at least one moiety comprising: at least one polyorganosiloxane group comprising, preferably, from 1 to about 10,000 organosiloxane units in the chain of the moiety or in the form of a graft, and at least two groups capable of establishing hydrogen interactions.

According to preferred embodiments of the present invention, the polyorganosiloxane-containing polymers used in the composition of the invention may belong to the following two families:
a) polyorganosiloxanes comprising at least two groups capable of establishing hydrogen interactions, these two groups being located in the polymer chain; and/or
b) polyorganosiloxanes comprising at least two groups capable of establishing hydrogen interactions, these two groups being located on grafts or branches.

The polyorganosiloxane containing polymers of the present invention can be liquid or solid at room temperature. Preferably, the polymers are solid. When the polymers are solid, it is preferable that they can be dissolved before or during use in a solvent with hydrogen interaction capable of breaking the hydrogen interactions of the polymers, for instance $C_2$ to $C_8$ lower alcohols and especially ethanol, n-propanol or isopropanol. It is also possible to use these hydrogen interaction "breaking" solvents as co-solvents in the compositions of the present invention. These solvents may then be stored in the composition or may be removed by selective evaporation, which is well known to those skilled in the art.

The polymers comprising two groups capable of establishing hydrogen interactions in the polymer chain may be polymers comprising at least one moiety corresponding to the formula:

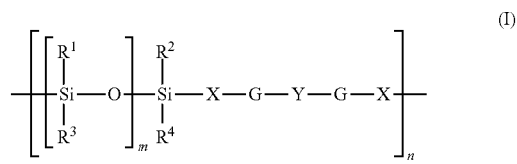

(I)

in which:
1) $R^1$, $R^2$, $R^3$ and $R^4$, which may be identical or different, represent a group chosen from:
linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may be linked to another chain of the polymer;

5) the groups G, which may be identical or different, represent divalent groups chosen from:

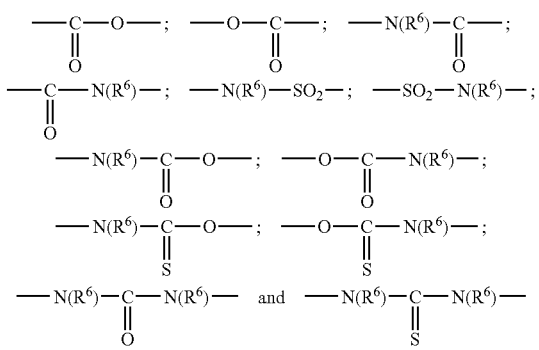

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

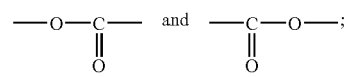

6) n is an integer of at least 1, for example ranging from 2 to 500 and preferably from 2 to 200, and m is an integer of at least one, ranging from 1 to 35,000, for example, from 1 to 10,000 and 1 to 2,500, from 1 to 700 and from 6 to 200, including all values and subranges there between.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) $C_{30}$ to $C_{56}$ branched alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

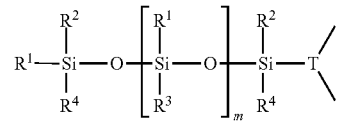

in which $R^1$, $R^2$, $R^3$, $R^4$, T and m are as defined above, and h) polyorganosiloxane chains of formula:

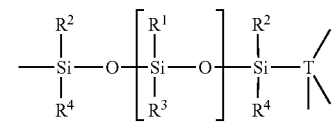

The polyorganosiloxanes of the second family may be polymers comprising at least one moiety corresponding to formula (II):

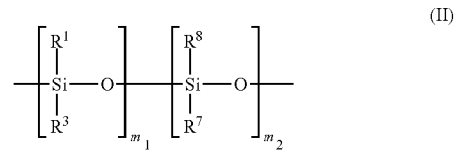

in which $R^1$ and $R^3$, which may be identical or different, are as defined above for formula (I), R[7] represents a group as defined above for R[1] and R[3], or represents a group of formula —X-G-R[9] in which X and G are as defined above for formula (I) and R[9] represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, R[8] represents a group of formula —X-G-R[9] in which X, G and R[9] are as defined above, $m_1$ is an integer of at least one ranging from 1 to 35,000, for example, from 1 to 10,000 and 1 to 2,500, from 1 to 700, and from 6 to 200, including all values and subranges there between; and $m_2$ is an integer of at least one ranging from 1 to 35,000, for example, from 1 to 10,000 and 1 to 2,500, from 1 to 700, and from 6 to 200, including all values and subranges there between.

According to the invention, the polyorganosiloxane containing polymer may be a homopolymer, that is to say a polymer comprising several identical moieties, in particular moieties of formula (I) or of formula (II).

According to the invention, it is also possible to use a polymer consisting of a copolymer comprising several different moieties of formula (I), that is to say a polymer in which at least one of the groups R[1], R[2], R[3], R[4], X, G, Y, m and n is different in one of the moieties. The copolymer may also be formed from several moieties of formula (II), in which at least one of the groups R[1], R[3], R[7], R[8], $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to preferred embodiments, it is also possible to use a copolymer comprising at least one hydrocarbon-based moiety comprising two groups capable of establishing hydrogen interactions, chosen from ester, amide, sulphonamide, carbamate, thiocarbamate, urea and thiourea groups, and combinations thereof.

These copolymers may be block copolymers or grafted copolymers.

According to a first embodiment of the invention, the groups capable of establishing hydrogen interactions are amide groups of formulae —C(O)NH— and —HN—C(O)—.

In this case, the polymer may comprise at least one moiety of formula (III) or (IV):

(III)

(IV)

in which R[1], R[2], R[3], R[4], X, Y, m and n are as defined above. Such a moiety may be obtained:

either by a condensation reaction between a silicone containing □, ω-carboxylic acid ends and one or more diamines, according to the following reaction scheme:

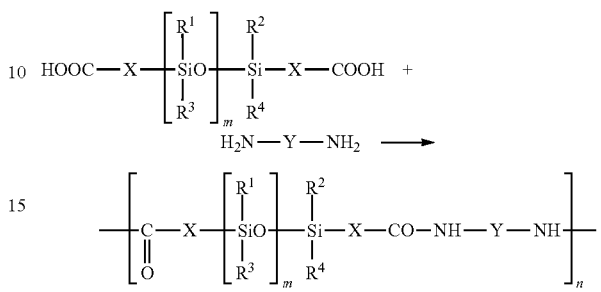

or by reaction of two molecules of □-unsaturated carboxylic acid with a diamine according to the following reaction scheme:

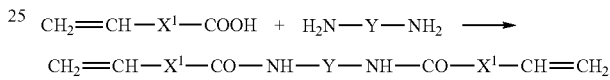

followed by the addition of a siloxane to the ethylenic unsaturations, according to the following scheme:

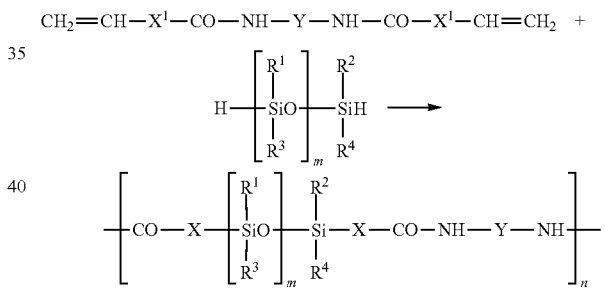

in which $X^1$—$(CH_2)_2$— corresponds to X defined above and Y, R[1], R[2], R[3], R[4] and m are as defined above;

or by reaction of a silicone containing □,ω-$NH_2$ ends and a diacid of formula HOOC—Y—COOH according to the following reaction scheme:

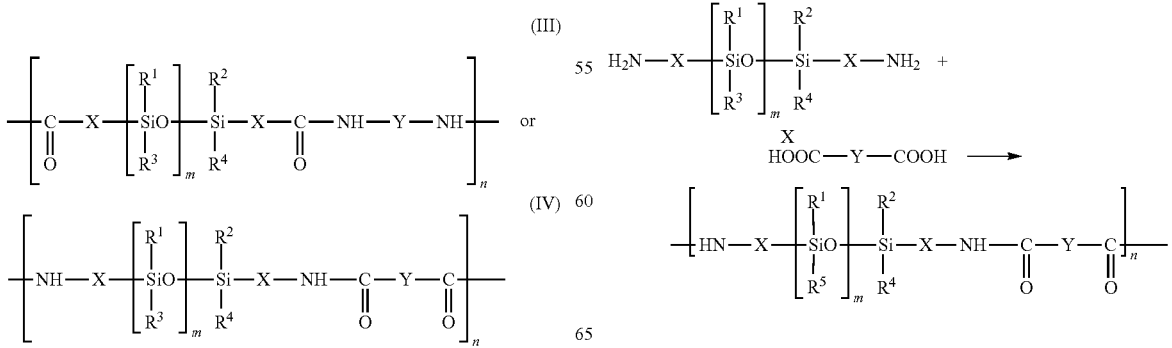

In these polyamides of formula (III) or (IV), m is an integer of at least one as defined above, and preferably in the range from 1 to 700, for example, from 15 to 500 and from 15 to 45, including all values and subranges there between; and n is in particular in the range from 1 to 500, for example, from 1 to 100 and from 4 to 25, including all values and subranges there between; X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, including from 1 to 20 carbon atoms and from 2 to 6 carbon atoms, including all values and subranges there between, for example, 6 carbon atoms.

In formulae (III) and (IV), the alkylene group representing X or Y can optionally contain in its alkylene portion at least one of the following elements:
1) 1 to 5 amide, urea or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one element chosen from the group consisting of:
a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^5$ represents a polyorganosiloxane chain and T represents a group of formula:

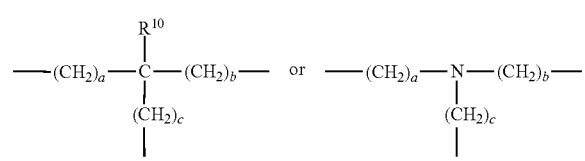

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

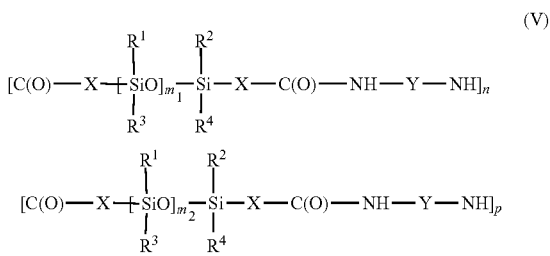

in which X, Y, n and $R^1$ to $R^4$ have the meanings given above, $m_1$ and $m_2$, which are different, are as defined above, and preferably are chosen in the range from 1 to 1 000, and p is at least one for example ranging from 2 to 500 and preferably from 2 to 200.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

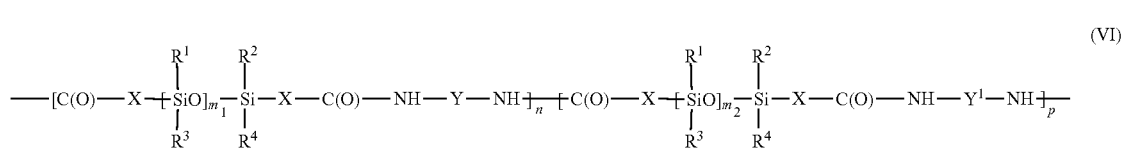

in which $R^1$ to $R^4$, X, Y, $m_1$, $m_2$, n and p have the meanings given above and $Y^1$ is different from Y but chosen from the groups defined for Y. As previously discussed, the various moieties may be structured to form either a block copolymer, or a random copolymer or an alternating copolymer.

In an embodiment of the invention, the polyorganosiloxane-containing polymer may also contain a grafted copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

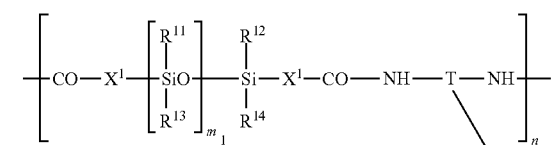

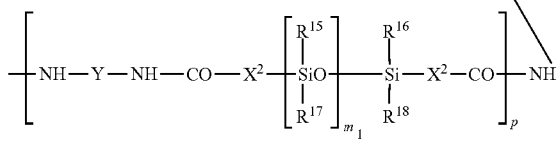

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1,000, and p is an integer of at least one, for example, p can range from 2 to 500.

In formula (VII), it is preferred that:
p is in the range from 1 to 25, including from 1 to 7, including all values and subranges there between,
$R^{11}$ to $R^{18}$ are methyl groups,
T corresponds to one of the following formulae:

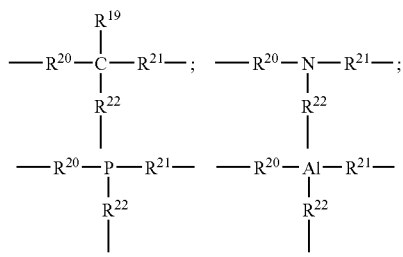

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

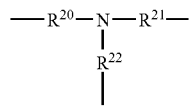

in particular with $R^{20}$, $R^{21}$ and $R^{22}$ representing —$CH_2$—$CH_2$—,
$m_1$ and $m_2$ are in the range from 15 to 500, including from 15 to 45 and including all values and subranges there between,
$X^1$ and $X^2$ represent —$(CH_2)_{10}$—, and
Y represents —$CH_2$—.

These polyamides containing a grafted silicone moiety of formula (VII) may be copolymerized with polyamide-silicones of formula (II) to form block copolymers, alternating copolymers or random copolymers.

The weight percentage of grafted silicone moieties (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:
polyamides of formula (III) in which m is from 15 to 300, for example, 15 to 100, including all values and subranges there between;
mixtures of two or more polyamides in which at least one polyamide has a value of m in the range from 15 to 50, including all values and subranges there between and at least one polyamide has a value of m in the range from 30 to 300, including all values and subranges there between;
polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1% to 99% by weight of the total weight of the polyamide;
mixtures of polyamide of formula (III) combining
1) 80% to 99% by weight of a polyamide in which n is equal to 2 to 10 and in particular 3 to 6, and
2) 1% to 20% of a polyamide in which n is in the range from 5 to 500 and in particular from 6 to 100;
polyamides corresponding to formula (VI) in which at least one of the groups Y and $Y^1$ contains at least one hydroxyl substituent;
polyamides of formula (III) synthesized with at least one portion of an activated diacid (diacid chloride, dianhydride or diester) instead of the diacid;
polyamides of formula (III) in which X represents —$(CH_2)_3$— or —$(CH_2)_{10}$; and
polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:
a $C_1$ to $C_{50}$ alkyl ester group by introducing a $C_1$ to $C_{50}$ monoalcohol during the synthesis,
a $C_1$ to $C_{50}$ alkylamide group by taking as stopping group a monoacid if the silicone is ☐,ω-diaminated, or a monoamine if the silicone is an ☐,ω-dicarboxylic acid.

According to one embodiment of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based polymers containing silicones may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and for example, 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a gelling agent based on a copolymer between a hydrocarbon-based polyamide and a silicone polyamide, by transamidation of a polyamide having, for example, an ethylene-diamine constituent, with an oligosiloxane-□,ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:
- by hydrosilylation of unsaturated bonds in polyamides based on fatty acid dimers;
- by silylation of the amide groups of a polyamide; or
- by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

The polyorganosiloxane containing polymers used in the composition of the invention are, most preferably polymers of the polyorganosiloxane type such as those described in documents U.S. Pat. Nos. 5,874,069, 5,919,441, 6,051,216 and 5,981,680, the entire disclosures of which are hereby incorporated by reference.

According to another embodiment of the invention, the polyorganoxilosane containing polymer is a homopolymer or a copolymer comprising urethane or urea groups.

As previously discussed, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

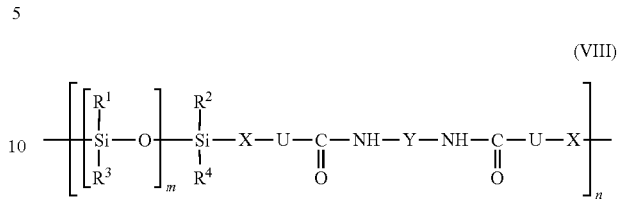

in which $R^1$, $R^2$, $R^3$, $R^4$, X, Y, m and n have the meanings given above for formula (I), and U represents —O— or —NH—, such that:

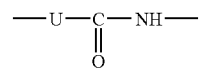

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

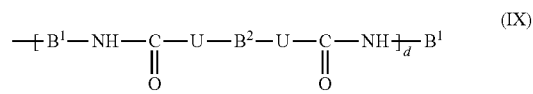

in which $B^1$ is a group chosen from the groups given above for Y, U is —O— or —NH— and $B^2$ is chosen from:

- linear or branched $C_1$ to $C_{40}$ alkylene groups, which can optionally bear an ionizable group such as a carboxylic acid or sulphonic acid group, or a neutralizable or quaternizable tertiary amine group,
- $C_5$ to $C_{12}$ cycloalkylene groups, optionally bearing alkyl substituents, for example one to three methyl or ethyl groups, or alkylene, for example the diol radical: cyclohexanedimethanol,
- phenylene groups that may optionally bear $C_1$ to $C_3$ alkyl substituents, and
- groups of formula:

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

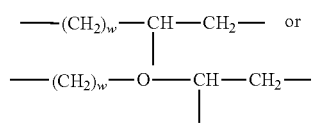

with w being an integer ranging from 1 to 10 and $R^5$ being a polyorganosiloxane chain.

When Y is a linear or branched $C_1$ to $C_{40}$ alkylene group, the $-(CH_2)_2-$ and $-(CH_2)_6-$ groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular $-(CH_2)_2-$ or $-(CH_2)_6-$ or a group:

with $R^5$ being a polyorganosiloxane chain.

As previously discussed, the polyorganosiloxane containing polymer may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

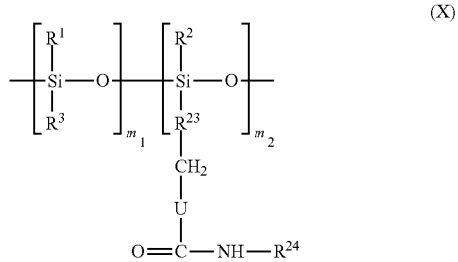

(X)

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used, for example, as gelling agents in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

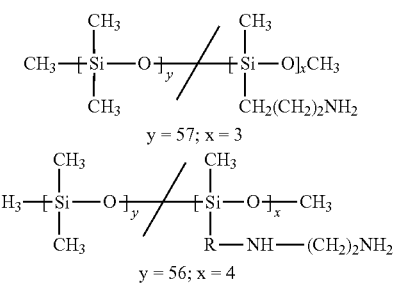

$y = 57; x = 3$ $y = 56; x = 4$

In these formulae, the symbol "/" indicates that the segments may be of different lengths and in a random order, and R represents a linear aliphatic group preferably containing 1 to 6 carbon atoms, including 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

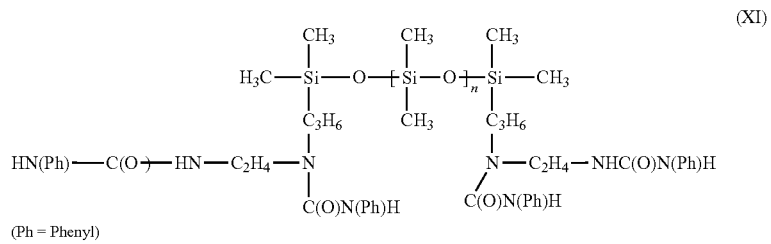

(XI)

(Ph = Phenyl)

in which Ph is a phenyl group and n is a number larger than 0, which includes, at least 1, 2 to 500, 2 to 200, from 1 to 300, in particular from 1 to 100, and all values and subranges there between, for example 50.

This polymer is obtained by reacting the following polysiloxane containing amino groups:

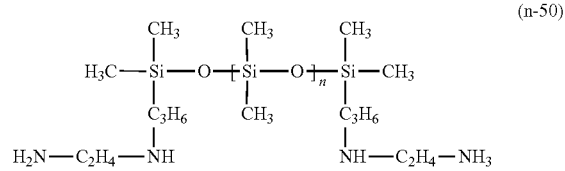

(n-50)

with phenyl isocyanate.

The polymers of formula (VIII) comprising urea or urethane groups in the chain of the silicone polymer may be obtained by reaction between a silicone containing □,ω-$NH_2$ or —OH end groups, of formula:

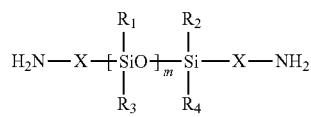

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^2$—$NH_2$ or HO—$B^2$—OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

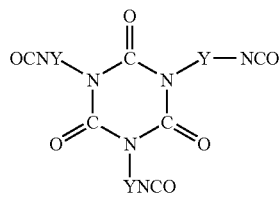

A polyurethane or polyurea silicone containing branches comprising an organosiloxane chain with groups capable of establishing hydrogen interactions is thus obtained. Such a polymer comprises, for example, a moiety corresponding to the formula:

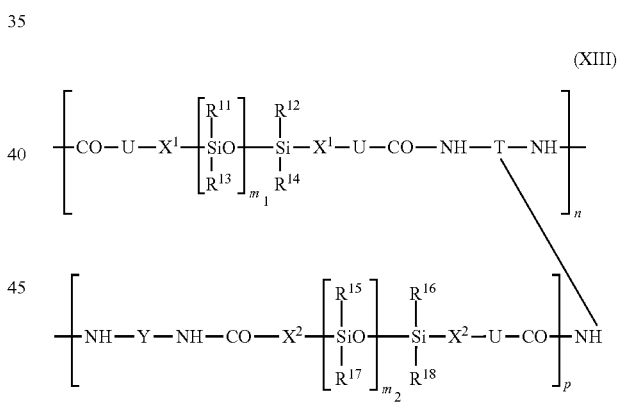

(XIII)

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are as defined above.

(XII)

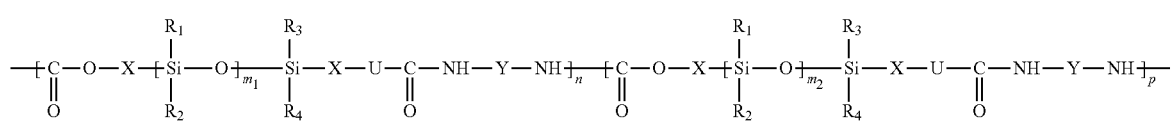

As in the case of the polyamides, this copolymer can also comprise polyurethane silicone moieties without branching.

In another embodiment of the invention, the siloxane-based polyureas and polyurethanes that are preferred are:

polymers of formula (VIII) in which m is from 15 to 300, for example, 15 to 100 and all values and subranges there between;

mixtures of two or more polymers in which at least one polymer has a value of m in the range from 15 to 50 and at least one polymer has a value of m in the range from 30 to 300, including all values and subranges there between;

polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;

mixtures of polymer of formula (VIII) combining
1) 80% to 99% by weight of a polymer in which n is equal to 2 to 10 and in particular 3 to 6, and
2) 1% to 20% of a polymer in which n is in the range from 5 to 500 and in particular from 6 to 100, copolymers comprising two moieties of formula (VIII) in which at least one of the groups Y contains at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a multifunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an □ω-difunctional block of non-silicone nature, for example a polyester, a polyether or a polyolefin.

As has been seen previously, homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

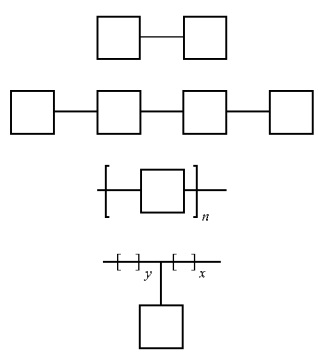

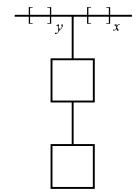

in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. Preferably, the values n, x and y are such that the polymer has the desired properties in terms of an agent for gelling fatty phases, preferably fatty phases based on silicone oil.

As examples of polymers that may be used, mention may be made of the silicone polyamides obtained in accordance with the disclosure in U.S. Pat. No. 5,981,680, the entire disclosure of which is hereby incorporated by reference.

Further examples of polyorganosiloxane containing polymers are set forth in U.S. Pat. Nos. 6,503,632 and 6,569,955, both of which are hereby incorporated by reference in their entirety.

As noted above, the polymers of the present invention can be solid or liquid at room temperature. When solid, the polymers preferably have a softening point from 50 to 130° C. Most preferably, they have a softening point ranging from 65 to 150° C., including from 70° C. to 130° C. This softening point is lower than that of other structuring polymers, which facilitates the use of the polymers that are the subject of the invention, and limits the deteriorations of the liquid fatty phase.

As noted above, the polyorganosiloxane containing polymers of the present invention contain both siloxane units and at least two groups capable of establishing hydrogen interactions such as amide linkages. The siloxane units can provide compatibility with a silicone fluid, if present, (for example with the cyclomethicones), while the groups capable of establishing hydrogen interactions and the spacing and selection of the locations of the amide linkages can facilitate gelation and the formation of cosmetic products.

According to preferred embodiments, the oil soluble film forming agent is present in the make-up composition in an amount effective to provide transfer resistant properties to the composition. Preferably, the film forming agent also provides at least one of the following properties to the composition: pliability, softness, wearing comfort, flexibility, adherence and non-tackiness.

In the make-up compositions, the oil soluble film forming agents are preferably present in an amount of 0.1-80 percent by weight, more preferably from 0.5 to 30 percent by weight, even more preferably from to 25 percent by weight and most preferably from 10 to 20 percent by weight of the total weight of the composition. One of ordinary skill in the art will recognize that the oil-soluble film forming agent may be commercially available, and may come from suppliers in the form of a dilute solution. In such case, the amounts of the oil soluble film forming agent disclosed herein therefore reflect the weight percent of active material. All numerical ranges and subranges are included within the numerical ranges identified above.

According to preferred embodiments of the present invention, the long wearing or transfer resistant make-up composition also comprises at least one coloring agent.

In the make-up composition, any coloring agent can be used. The at least one coloring agent is preferably chosen from pigments, dyes such as liposoluble dyes, nacreous pigments, and/or pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, most preferably from 0.0001% to 6%.

The nacreous pigments which may be used according to the present invention include but are not limited to nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%. In the case of certain products, the pigments, including nacreous pigments, may, for example, represent up to 50% by weight of the composition.

The make-up composition of the invention can also optionally comprise any additive usually used in such compositions. For example, oils (volatile and nonvolatile), organogelators, dispersants, antioxidants, vitamins, emollients, preserving agents, fragrances, waxes, fillers, neutralizing agents, cosmetic and dermatological active agents, moisturizers, humectants, water, sunscreen agents, gelling agents, elastomers, short chain esters, surfactants, plasticizers, and mixtures thereof can be added, if desired. Further examples of suitable optional components can be found in the references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the compositions, kits and methods according to the invention are not, or are not substantially, adversely affected by the envisaged addition.

These substances may be selected variously by the person skilled in the art in order to prepare a composition which has the desired properties, for example, consistency or texture. For example, ingredients such as phenylated silicone oils can be added to enhance shine, gellants such as kaolin and/or elastomers can be added to enhance sensory effects, lauroyl lysine can be added to enhance the satin finish of the product. The product's stability can also be enhanced through addition of known stabilizers such as polymethylmethacrylate. Also, fillers such as nylon-12, HDI/Trimethylol hexyllactone crosspolymer, and polyethylene are preferably added.

Such additives may be present in the composition in a proportion from 0% to 90% relative to the total weight of the composition, preferably from 0.01% to 85%, and most preferably from 10 to 80% (if present).

The make-up composition can be either solid (for example, a lipstick or a foundation stick) or liquid (for example, a liquid lip composition, mascara, liquid foundation or nail polish). Also, the make-up composition can contain water, but it also may be anhydrous, if desired.

Removal Composition

According to preferred embodiments of the present invention, the removal composition comprises at least one oil soluble film forming agent and at least one oil.

In the removal composition, any oil soluble film forming agent can be used. Suitable oil soluble film forming agents are discussed above in connection with the make-up composition. Preferably, the oil soluble film forming agent in the removal composition is a polyorganosiloxane-containing copolymer, most preferably a polyorganosiloxane-containing copolymer comprising at least one hydrocarbon-based moiety comprising an amide group such as, for example, a Nylon-611/dimethicone copolymer.

In the removal compositions, the oil soluble film forming agents are preferably present in an amount of 0.1-80 percent by weight, more preferably from 0.5 to 30 percent by weight, even more preferably from 5 to 25 percent by weight and most preferably from 10 to 20 percent by weight of the total weight of the composition. One of ordinary skill in the art will recognize that the oil-soluble film forming agent may be commercially available, and may come from suppliers in the form of a dilute solution. In such case, the amounts of the oil soluble film forming agent disclosed herein therefore reflect the weight percent of active material. All numerical ranges and subranges are included within the numerical ranges identified above.

In a preferred embodiment, the oil soluble film-forming agent in the make-up composition and the oil soluble film-forming agent in the removal composition are the same film-forming agent.

In another preferred embodiment, the oil soluble film forming agent in both the make-up composition and the removal composition are polyorganosiloxane-containing copolymers, most preferably a polyorganosiloxane-containing copolymer comprising at least one hydrocarbon-based moiety comprising an amide group such as, for example, a Nylon-611/dimethicone copolymer.

According to preferred embodiments of the present invention, the removal composition comprises at least one oil. The at least one oil may be, independently or in combinations, volatile silicone oils, non-volatile silicone oils, volatile non-silicone oils and non-volatile non-silicone oils. In a preferred embodiment, the removal composition of the present invention is substantially free of volatile oils (i.e., contains less than about 5% volatile oil). In another embodiment, the removal compositions are essentially free of volatile oils (i.e., contain less than about 1% volatile oil). In another embodiment, the compositions are free of volatile oils (i.e., contain less than about 0.1% volatile oil).

Preferably, the at least one oil is a non-volatile oil. Suitable non-volatile oils include, but are not limited, non-volatile silicone oils such as, for example, non-volatile linear polydimethylsiloxanes (PDMSs) such as dimethicones; polydimethylsiloxanes comprising alkyl, alkoxy or phenyl groups, which are pendent and/or at the end of a silicone chain, these groups each containing from 2 to 24 carbon atoms; and phenylated silicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

Suitable non-silicone, non-volatile oils which can be used in the removal compositions of the present invention include polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol; and mixtures thereof.

Preferably, the at least one oil represents from 5% to 90% of the total weight of the removal composition, more preferably from 10% to 80% of the total weight of the composition, and most preferably from 20% to 75%.

According to a particularly preferred embodiment, the removal composition further comprises at least one crosslinked elastomeric polyorganosiloxane. These elastomeric silicones can bear hydrophile groups, such as polyoxyethylene or copoly(oxyethylene/oxypropylene), if desired. These elastomeric silicones may also optionally have hydrophile groups in the crosslinking chain.

Suitable crosslinked elastomeric polyorganosiloxanes include, but are not limited to, the crosslinked elastomeric polyorganosiloxanes described in application EP-A-0,295, 886, the disclosure of which is incorporated herein by reference. According to that application, the elastomers are obtained by addition reaction and crosslinking, in the presence of a platinum-type catalyst, of at least:

(a) a polyorganosiloxane having at least two $C_2$ to $C_6$ lower alkenyl groups per molecule; and
(b) a polyorganosiloxane having at least two hydrogen atoms linked to a silicon atom per molecule.

Suitable elastomers also include but are not limited to those described in U.S. Pat. No. 5,266,321, the disclosure of which is incorporated by reference herein. According to that patent, the elastomers are chosen in particular from:

i) polyorganosiloxanes comprising $R_2SiO$ and $RSiO_{1.5}$ units and optionally $R_3SiO_{0.5}$ and/or $SiO_2$ units in which the radicals R, independently of each other, are chosen from a hydrogen, an alkyl such as methyl, ethyl or propyl, an aryl such as phenyl or tolyl, an unsaturated aliphatic group such as vinyl, the weight ratio of the units $R_2SiO$ to the units $RSiO_{1.5}$ ranging from 1/1 to 30/1;

ii) polyorganosiloxanes which are insoluble and swellable in silicone oil, obtained by addition of an polyorganohydrogenosiloxane (1) and of a polyorganosiloxane (2) having unsaturated aliphatic groups such that the amount of hydrogen or of unsaturated aliphatic groups in (1) and (2) respectively ranges from 1 to 20 mol % when the polyorganosiloxane is non-cyclic and from 1 to 50 mol % when the polyorganosiloxane is cyclic. Optionally, these polyorganosiloxanes can comprise from 1 to 40 oxyalkylene groups, such as oxypropylene and/or oxyethylene groups.

Specific examples of elastomeric polyorganosiloxanes which can be used according to the invention include those sold or made under the names KSG6 from Shin-Etsu, Trefil E-505C, Trefil E-506C, DC 9506 or DC 9701 from Dow-Corning, Gransil from Grant Industries (SR-CYC, SR DMF10, SR-DC556) or those marketed in the form of pre-constituted gels (DC9040, DC9041 from Dow Corning, KSG15, KSG17, KSG16, KSG18, KSG21 from Shin-Etsu, Gransil SR 5CYC gel, Gransil SR DMF 10 gel, Gransil SR DC556 gel, SF 1204 and JK 113 from General Electric) or emulsifying elastomers such as those sold under the names of KSG-210, KSG-30, KSG-31, KSG-32, KSG-33, KSG-40, KSG 41, KSG-42, KSG-43, KSG-44 and KSG-710 from Shin-Etsu, or coated elastomers such as products sold under the denomination KSP (for example, KSP100, KSP 200, KSP 300) sold by Shin Etsu and/or those described in U.S. Pat. No. 5,538,793, the disclosure of which is hereby incorporated by reference. A mixture of these commercial products may also be used.

In the removal compositions, the crosslinked elastomeric polyorganosiloxanes are preferably present in an amount of 0.1-25 percent by weight, more preferably from 0.5 to 20 percent by weight, even more preferably from 1 to 15 percent by weight and most preferably from 3 to 10 percent by weight of the total weight of the composition. One of ordinary skill in the art will recognize that the crosslinked elastomeric polyorganosiloxane may be commercially available, and may come from suppliers in the form of a dilute solution. In such case, the amounts of the crosslinked elastomeric polyorganosiloxane disclosed herein therefore reflect the weight percent of active material. All numerical ranges and subranges are included within the numerical ranges identified above.

The removal composition of the invention can also optionally comprise any additive usually used in cosmetic compositions. Suitable optional ingredients (and amounts thereof) are discussed above in connection with the make-up composition. Particularly preferred optional ingredients are exfoliating agents. Suitable exfoliating agents include but are not limited to fillers or other solid agents such as polyethylene, sugars, ground fruit kernels, diatomaceous earth, metal oxides, etc.

In accordance with preferred embodiments of the present invention, removal of the make-up composition from keratin material such as skin, lips, nails or eyelashes is effected by applying to the make-up composition a removal composition comprising at least one oil soluble film-forming agent and at least one oil. By applying the removal composition "to the make-up composition," what is meant is that the removal composition is applied on top of the make-up composition either directly or indirectly. Direct application would be application to the make-up composition itself. Indirect application would be application to a composition such as, for example, a gloss or a topcoat composition, which had previously been applied to the make-up composition.

After such direct or indirect application, the user allows the removal composition to remain on the make-up composition for a short period of time (preferably less than 5 minutes, most preferably between about 1 and about 2 minutes). After this short period of time, the user removes the removal composition by wiping, rubbing, etc. the keratin material until the make-up composition has been removed. Preferably, such wiping or rubbing is performed with a disposable or non-disposable towel, cloth or tissue. Subsequently, the keratin material can be rinsed with water or cleaned using typical cleansing materials, if desired, although such rinsing or cleansing is optional.

Alternatively, instead of placing the removal composition onto the make-up composition, the removal composition can be placed onto or into (for example, impregnated) the towel, cloth or tissue used to wipe, rub, etc. the make-up composition. Then, the removal composition-containing towel, cloth or tissue can be used to wipe or rub the make-up composition. In this embodiment, more rubbing or wiping may be needed to remove the make-up composition than in the embodiment where the removal composition is applied to the make-up composition.

In accordance with yet another embodiment of the present invention, kits comprising a transfer-resistant or long wearing make-up composition comprising at least one oil soluble film-forming agent and at least one coloring agent and a removal composition comprising at least one oil soluble film-forming agent and at least one oil are provided. In this embodiment, the make-up composition and the removal composition are those described above. In addition to these two compositions, the kits of the present invention can further comprise one or more compositions such as, for example, compositions to be applied on top of the make-up composition (glosses or topcoats), and/or compositions to be applied underneath the make-up composition (primers or basecoats). Any suitable topcoat or basecoat can be included in such kits.

The packaging and application device for any such kit or compositions in the kit may be chosen and manufactured by persons skilled in the art on the basis of their general knowledge, and adapted according to the nature of the compositions to be packaged. Indeed, the type of device to be used can be in particular linked to the consistency of the composition, in particular to its viscosity; it can also depend on the nature of the constituents present in the compositions.

In accordance with yet another embodiment of the present invention, methods for applying gloss to keratin materials comprising applying a gloss composition comprising at least one oil soluble film-forming agent, at least one oil and at least one coloring agent to the keratin material in an amount sufficient to provide gloss to the keratin material are also provided. In the gloss composition, any oil soluble film forming agent, any oil and any coloring agent can be used. Suitable oil soluble film forming agents, oils and coloring agents are discussed above in connection with the make-up and removal compositions.

According to this embodiment, the gloss composition is applied topically to the desired keratin material in an amount sufficient to provide gloss to the keratinous material. The gloss compositions may be applied to the desired area as needed, preferably once or twice daily, more preferably once daily and then preferably allowed to dry before subjecting to contact such as with clothing or other objects. The gloss composition is preferably applied to the desired area that is dry or has been dried prior to application.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1

Make-up Composition

| Quantity | Raw |
| --- | --- |
| 5-20 | MQ RESIN (TRIMETHYLSILOXYSILICATE) |
| 5-20 | NYLON-611/DIMETHICONE COPOLYMER |
| 1-4 | DISTEARDIMONIUM HECTORITE |
| 0.25-1.25 | PROPYLENE CARBONATE |
| As needed | FRAGRANCE |
| 5-20 | Pigments/fillers |
| Qs 100 | ISODODECANE |

Other suitable make-up compositions are described in U.S. patent application publication no. 2004-0170586, corresponding to U.S. patent application Ser. No. 10/733,467, filed Dec. 10, 2003, hereby incorporated by reference in its entirety.

EXAMPLE 2

Removal Compositions

| INGREDIENT | FORMULATION 1 | FORMULATION 2 |
| --- | --- | --- |
| BHT | 0.05 | 0.05 |
| HYDROGENATED JOJOBA OIL | | 0.33 |

-continued

| INGREDIENT | | |
|---|---|---|
| PIGMENTS/FILLERS | 7.51 | 9.27 |
| PRESERVATIVES | 0.6 | 0.6 |
| CYCLOPENTASILOXANE | | 23.61 |
| PHENYL TRIMETHICONE | 8.3 | 7.93 |
| DIMETHICONE (5 CsT) | 52.92 | 30.52 |
| CYCLOPENTASILOXANE (and) DIMETHICONE CROSSPOLYMER (DC 5930) | 15.31 | 14.46 |
| NYLON-611/ DIMETHICONE COPOLYMER | 11.48 | 9.56 |
| C12-15 ALKYL BENZOATE | 3.83 | 3.54 |
| STEARYL ALCOHOL | | 0.19 |

| INGREDIENT | FORMULATION 3 |
|---|---|
| PIGMENTS/FILLERS | 10.28 |
| PHENYL TRIMETHICONE | 8.05 |
| DIMETHICONE | 51.96 |
| CYCLOPENTASILOXANE (and) DIMETHICONE CROSSPOLYMER (DC 5930) | 14.85 |
| NYLON-611/ DIMETHICONE COPOLYMER | 11.14 |
| C12-15 ALKYL BENZOATE | 3.72 |

What is claimed is:

1. A method for removing a make-up composition from skin or lips, wherein the make-up composition comprises at least one silicone resin and at least one coloring agent, comprising applying to the make-up composition a removal composition comprising at least one nylon-611/dimethicone copolymer and at least one oil and removing the make-up composition from the skin or lips, wherein the removal composition is not in the form of a stick.

2. The method according to claim 1, wherein the make-up composition further comprises a polyorganosiloxane-containing copolymer.

3. The method according to claim 2, wherein the polyorganosiloxane-containing copolymer comprises at least one hydrocarbon-based moiety comprising an amide group.

4. The method according to claim 2, wherein the polyorganosiloxane-containing copolymer is a Nylon-611/dimethicone copolymer.

5. The method according to claim 1, wherein the silicone resin is an MQ resin.

6. The method according to claim 1, wherein the at least one oil in the removal composition is a silicone oil.

7. The method according to claim 6, wherein the silicone oil is dimethicone.

8. The method according to claim 6, wherein the silicone oil is a phenylated silicone oil.

9. The method according to claim 1, wherein the removal composition is free of volatile oil.

10. The method according to claim 1, wherein the nylon-611/dimethicone copolymer is present in an amount ranging from 0.5% to 30% by weight relative to the total weight of the removal composition.

11. The method according to claim 5, wherein the nylon-611/dimethicone copolymer is present in an amount ranging from 0.5% to 30% by weight relative to the total weight of the removal composition.

12. The method according to claim 1, wherein the make-up composition is liquid.

13. The method according to claim 1, wherein the make-up composition is anhydrous.

14. The method according to claim 1, wherein the removal composition further comprises a crosslinked elastomeric polyorganosiloxane.

15. The method according to claim 1, wherein the removal composition further comprises a coloring agent.

16. The method according to claim 1, wherein the make-up composition is a lip composition.

17. The method according to claim 1, wherein the make-up composition is a foundation.

18. The method according to claim 1, wherein the removal composition is in the form of a gel.

* * * * *